United States Patent
Oi et al.

(10) Patent No.: US 6,974,886 B2
(45) Date of Patent: Dec. 13, 2005

(54) PROCESS FOR PRODUCING DIHYDROXYDIPHENYLSULFONE

(75) Inventors: Fumio Oi, Wakayama (JP); Norio Yanase, Wakayama (JP); Takayuki Kitahara, Wakayama (JP); Nobuyuki Nate, Wakayama (JP)

(73) Assignee: Konishi Chemical Ind. Co., Ltd., Wakayama (JP)

( * ) Notice: Subject to any disclaimer, the term of this patent is extended or adjusted under 35 U.S.C. 154(b) by 0 days.

(21) Appl. No.: 10/511,823

(22) PCT Filed: Apr. 24, 2003

(86) PCT No.: PCT/JP03/05228

§ 371 (c)(1),
(2), (4) Date: Oct. 19, 2004

(87) PCT Pub. No.: WO03/091206

PCT Pub. Date: Nov. 6, 2003

(65) Prior Publication Data

US 2005/0171384 A1    Aug. 4, 2005

(30) Foreign Application Priority Data

Apr. 25, 2002   (JP) .............................. 2002-123646

(51) Int. Cl.$^7$ ............................................ C07C 317/33

(52) U.S. Cl. .................................................. 568/33
(58) Field of Search ......................................... 568/33

(56) References Cited

U.S. PATENT DOCUMENTS 6,700,020 B2 *   3/2004   Pabst et al. .................... 568/33

FOREIGN PATENT DOCUMENTS

| EP | 0 220 855 A1 | 5/1987 | |
|----|---|---|---|
| JP | 10 - 27277 A | 1/1998 | |
| JP | 10 - 139756 A | 5/1998 | |
| WO | WO 2001079163 | * 10/2001 | ......... C07C 315/00 |

* cited by examiner

Primary Examiner—Johann Richter
Assistant Examiner—Chukwuma Nwaonicha
(74) Attorney, Agent, or Firm—Knobbe, Martens, Olson & Bear LLP

(57) ABSTRACT

The present invention provides a process for producing dihydroxydiphenylsulfone wherein trihydroxytriphenylsulfone and coloring impurities are effectively removed without altering the isomeric composition of dihydroxydiphenylsulfone. In particular, the present invention provides a process for producing dihydroxydiphenylsulfone comprising the steps of dissolveing or suspending in an aqueous solvent crude dihydroxydiphenylsulfone containing trihydroxytriphenylsulfone, adjusting the pH to 5–7, optionally cooling, and separating the crystalline dihydroxydiphenylsulfone thus precipitated.

19 Claims, No Drawings

PROCESS FOR PRODUCING DIHYDROXYDIPHENYLSULFONE

This application is the U.S. National Phase under 35 U.S.C. §371 of International Application PCT/JP03/05228, filed Apr. 24, 2003, which claims priority to Japanese Patent Application No. 2002-123646, filed Apr. 25, 2002. The International Application was not published under PCT Article 21(2) in English.

TECHNICAL FIELD

The present invention relates to a process for producing dihydroxydiphenylsulfone.

BACKGROUND OF THE INVENTION 4,4'-Dihydroxydiphenylsulfone (hereinafter occasionally referred to as 4,4'-DDS), 2,4'-dihydroxydiphenylsulfone (hereinafter occasionally referred to as 2,4'-DDS) and mixtures thereof are of use as materials for engineering polymers, color developers for heat-sensitive paper, and the like. Trihydroxytriphenyldisulfone (hereinafter occasionally referred to as TTDS) and coloring impurities generated during the reactions for producing dihydroxydiphenylsulfone cause the properties of dihydroxydiphenylsulfone to be impaired. Therefore, a process for the effective removal thereof has been sought.

DISCLOSURE OF THE INVENTION

An object of the present invention is to provide a process for producing dihydroxydiphenylsulfone wherein TTDS and coloring impurities are effectively removed without altering the isomeric composition of dihydroxydiphenylsulfone.

The present invention provides processes for producing dihydroxydiphenylsulfone as presented below:

Item 1. A process for producing dihydroxydiphenylsulfone comprising the steps of:
dissolving or suspending crude dihydroxydiphenylsulfone containing trihydroxytriphenylsulfone in an aqueous solvent;
adjusting the pH of the aqueous solvent to 5–7;
optionally cooling the aqueous solvent; and
separating the precipitated crystalline dihydroxydiphenylsulfone.

Item 2. A process for producing dihydroxydiphenylsulfone comprising the steps of:
dissolving or suspending crude dihydroxydiphenylsulfone containing trihydroxytriphenylsulfone in an aqueous solvent by adding alkali;
adjusting the pH of the aqueous solvent to 5–7 by adding an acidic substance;
optionally cooling the aqueous solvent; and
separating the precipitated crystalline dihydroxydiphenylsulfone.

Item 3. The process for producing dihydroxydiphenylsulfone according to Item 1 or 2, wherein the pH is adjusted to 6 or greater and less than 7.

Item 4. The process for producing dihydroxydiphenylsulfone according to any one of Items 1–3, wherein the crude dihydroxydiphenylsulfone contains trihydroxytriphenylsulfone in a proportion of 30 wt. % or less.

Item 5. The process for producing dihydroxydiphenylsulfone according to any one of Items 1–4, wherein the crystalline dihydroxydiphenylsulfone is separated at 60° C. or lower.

It is essential to the present invention to adjust the pH of the aqueous solvent in which TTDS-containing crude dihydroxydiphenylsulfone is dissolved or suspended to 5–7. Thus, pH adjustment is not particularly necessary if, for example, the aforementioned pH range is satisfied merely by introducing TTDS-containing crude dihydroxydiphenylsulfone into an aqueous solvent. The scope of the invention includes such an embodiment.

The starting material of the present invention, i.e., TTDS-containing crude dihydroxydiphenylsulfone, is not limited, and usable are solvent-containing dihydroxydiphenylsulfone reaction products, such a reaction product dried to remove solvent, such a reaction product from which sulfonic acids have been removed, a solution prepared by the addition of a basic aqueous solution to such a reaction product and the extraction of dihydroxydiphenylsulfone isomers therefrom, a commercially available crude product containing an isomeric mixture, etc.

The crude dihydroxydiphenylsulfone preferably contains TTDS in a proportion of 30 wt. % or less, and more preferably 20 wt. % or less. The weight ratio of 2,4'-DDS to 4,4'-DDS in the crude dihydroxydiphenylsulfone is not limited, and it is preferably 2,4'-DDS/4,4'-DDS=0/100 to 99/1, and more preferably 0.1/99.9 to 98/2.

Moreover, crude dihydroxydiphenylsulfone usable herein may contain other impurities such as sulfonic acids, reaction solvents, etc.

Water is preferable as the aqueous solvent used in the present invention. Water may contain a water-miscible solvent in a proportion of 40 wt. % or less, such as methanol, ethanol, isopropyl alcohol or like $C_{1-3}$ alcohol; acetone, methyl ethyl ketone or like ketone; ethylene glycol, diethylene glycol or like polyhydric alcohol; etc.

The amount of aqueous solvent to be used is preferably at most 20 times the weight of crude dihydroxydiphenylsulfone, preferably 0.5–10 times and particularly preferably 2–8 times.

Examples of alkalis usable in the present invention include LiOH, NaOH, KOH and like alkali metal hydroxides; $Li_2CO_3$, $Na_2CO_3$, $K_2CO_3$ and like alkali metal carbonates; $LiHCO_3$, $NaHCO_3$, $KHCO_3$ and like alkali metal bicarbonates; ammonia, triethylamine and like amine compounds; etc. Among these examples, alkali metal hydroxides are preferable, and NaOH is particularly preferable.

The amount of alkali to be used is preferably 2 equivalents or less relative to the total amount of 2,4'-DDS, 4,4'-DDS and TTDS, and more preferably 0.001–1 equivalents. The term "1 equivalent" herein refers to the amount of alkali necessary to convert 1 mol of 2,4'-DDS, 4,4'-DDS and TTDS in total to 1 mol of a mono alkali metal salt of 2,4'-DDS, 4,4'-DDS and TTDS. Therefore, when an alkali metal hydroxide, alkali metal bicarbonate or an amine compound is used as an alkali, the molar amount thereof is preferably no greater than twice the molar amount of 2,4'-DDS, 4,4'-DDS and TTDS contained in crude dihydroxydiphenylsulfone, and more preferably 0.001 times to equimolar. Moreover, when used as an alkali, an alkali metal carbonate is preferably used in no greater than equimolar relative to the molar amount of 2,4'-DDS, 4,4'-DDS and TTDS contained in crude dihydroxydiphenylsulfone, and more preferably 0.0005–0.5 times.

When crude dihydroxydiphenylsulfone contains sulfonic acids, it is preferable to add alkali in an amount sufficient to neutralize the sulfonic acids in addition to the amount described above.

The temperature for dissolving or suspending crude dihydroxydiphenylsulfone after adding alkali is preferably within the range of from room temperature to the boiling temperature of the solvent. Dissolution and suspension may be carried out under pressure, if necessary. Moreover, if necessary, the dissolved crude dihydroxydiphenylsulfone may be treated with activated carbon, and a reducing agent may be added to decolorize.

Subsequently, an acidic substance is added to the solution or suspension of crude dihydroxydiphenylsulfone. Examples of acidic substances include sulfuric acid, hydrochloric acid, nitric acid, phosphoric acid and like mineral acids, acetic acid and like organic acids, etc.

Once the solution or suspension is mixed with an acidic substance and, if necessary, cooled, a dihydroxydiphenylsulfone isomeric mixture composed of 2,4'-DDS and 4,4'-DDS precipitates. The pH of the solution or suspension in this instance is 5–7, preferably 6 or greater and less than 7, and more preferably 6.2–6.8. The precipitation temperature is preferably within the range of from room temperature to 90° C.

The precipitated crystalline dihydroxydiphenylsulfone isomeric mixture can be separated according to conventional solid-liquid separation techniques such as filtration (vacuum filtration, pressure filtration, centrifugation, etc.), decantation, etc. The temperature upon separating the crystals is preferably 60° C. or lower, more preferably 50° C. or lower, and particularly preferably 20–45° C.

The dihydroxydiphenylsulfone obtained according to the production process of the invention as described above contains TTDS in a proportion of 3 wt. % or less, more preferably 1 wt. % or less, and particularly preferably 0.2 wt. % or less.

Moreover, according to the production process of the invention, coloring impurities contained in crude dihydroxydiphenylsulfone can be highly effectively removed. For example, when the production process of the present invention is performed using crude dihydroxydiphenylsulfone having an APHA value of 1000–2000 in 5% acetone solution, the APHA value of the resulting dihydroxydiphenylsulfone is decreased to about 500 or less.

BEST MODE FOR CARRYING OUT THE INVENTION

Examples are given below to illustrate the process of the invention in more detail, but the scope of the invention is not limited to these examples.

EXAMPLE 1

To 100 g of crude dihydroxydiphenylsulfone isomeric mixture (APHA value of 1000 in 5% acetone solution) containing 75 wt. % 4,4'-DDS, 20 wt. % 2,4'-DDS and 5 wt. % TTDS (4,4'-DDS, 2,4'-DDS and TTDS totaling 0.39 mol) were added 300 g of water and 8 g of sodium hydroxide (0.2 mol; 0.5 times the total molar amount of 4,4'-DDS, 2,4'-DDS and TTDS), and heated to 90° C. to dissolve the isomeric mixture. The solution was mixed with 50% sulfuric acid at 50° C. to adjust the pH to 6.5. The solution was cooled to 35° C., and the crystals thus precipitated were filtered off, washed with water and dried, thereby giving 92 g of dried crystals. An HPLC analysis showed 78.9 wt. % 4,4'-DDS, 21.0 wt. % 2,4'-DDS and 0.1 wt. % TTDS. A 5% acetone solution thereof had an APHA value of 400.

EXAMPLE 2

The procedure described in Example 1 was repeated except for using 100 g of crude dihydroxydiphenylsulfone isomeric mixture (APHA value of 1500 in 5% acetone solution) containing 50 wt. % 4,4'-DDS, 40 wt. % 2,4'-DDS and 10 wt. % TTDS (4,4'-DDS, 2,4'-DDS and TTDS totaling 0.38 mol), thereby giving 89 g of dried crystals. An HPLC analysis showed 55.8 wt. % 4,4'-DDS, 44.0 wt. % 2,4'-DDS and 0.2 wt. % TTDS. A 5% acetone solution thereof had an APHA value of 500.

EXAMPLE 3

The procedure described in Example 1 was repeated except for using 100 g of crude dihydroxydiphenylsulfone isomeric mixture (APHA value of 1000 in 5% acetone solution) containing 95 wt. % 4,4'-DDS, 2 wt. % 2,4'-DDS and 3 wt. % TTDS (4,4'-DDS, 2,4'-DDS and TTDS totaling 0.40 mol), thereby giving 95 g of dried crystals. An HPLC analysis showed 98 wt. % 4,4'-DDS, 2 wt. % 2,4'-DDS and 0 wt. % TTDS. A 5% acetone solution thereof had an APHA value of 400.

EXAMPLE 4

To 100 g of crude dihydroxydiphenylsulfone isomeric mixture (APHA value of 1000 in 5% acetone solution) containing 69 wt. % 4,4'-DDS, 19 wt. % 2,4'-DDS and 12 wt. % TTDS (4,4'-DDS, 2,4'-DDS and TTDS totaling 0.38 mol) were added a mixed solution of 40 ml methanol and 360 ml water and 4.8 g of sodium hydroxide (0.12 mol; 0.3 times the total molar amount of 4,4'-DDS, 2,4'-DDS and TTDS), and heated to 80° C. to dissolve the isomeric mixture. The solution was mixed with sulfuric acid at 50° C. to adjust the pH to 6.7. The solution was cooled to 25° C., and the crystals thus precipitated were filtered off, washed with water and dried, thereby giving 80 g of dried crystals. An HPLC analysis showed 78 wt. % 4,4'-DDS, 22 wt. % 2,4'-DDS and 0 wt. % TTDS. A 5% acetone solution thereof had an APHA value of 300.

EXAMPLE 5

The procedure described in Example 1 was repeated except for using 100 g of crude dihydroxydiphenylsulfone isomeric mixture (APHA value of 1000 in 5% acetone solution) containing 17 wt. % 4,4'-DDS, 78 wt. % 2,4'-DDS and 5 wt. % TTDS (4,4'-DDS, 2,4'-DDS and TTDS totaling 0.39 mol), thereby giving 92 g of dried crystals. An HPLC analysis showed 17 wt. % 4,4'-DDS, 83 wt. % 2,4'-DDS and 0.1 wt. % TTDS. A 5% acetone solution thereof had an APHA value of 450.

Comparative Example 1

The procedure described in Example 1 was repeated except for reducing the amount of 50% sulfuric acid so as to give a pH of 7.5. Seventy nine grams of dried crystals were recovered, resulting in a 13 g decrease in yield compared with that of Example 1. An HPLC analysis showed 85 wt. % 4,4'-DDS, 15 wt. % 2,4'-DDS and 0 wt. % TTDS. A 5% acetone solution thereof had an APHA value of 200.

Comparative Example 2

The procedure described in Example 1 was repeated except for increasing the amount of 50% sulfuric acid so as to give a pH of 4.0. Ninety eight grams of dried crystals were recovered. An HPLC analysis showed 76 wt. % 4,4'-DDS, 19 wt. % 2,4'-DDS and 5 wt. % TTDS. A 5% acetone solution thereof had an APHA value of 1000. TTDS and coloring impurities were therefore barely removed.

INDUSTRIAL APPLICABILITY

According to the process of the present invention, TTDS and coloring impurities can be highly effectively removed using an aqueous solvent without altering the isomeric composition of dihydroxydiphenylsulfone. Moreover, the process gives an excellent dihydroxydiphenylsulfone recovery.

Furthermore, since organic solvents are not used, the process offers excellent workability, safety, ecology and economy.

What is claimed is:

1. A process for producing dihydroxydiphenylsulfone comprising the steps of:
   dissolving or suspending crude dihydroxydiphenylsulfone containing trihydroxytriphenylsulfone in an aqueous solvent;
   adjusting the pH of the aqueous solvent to 5–7;
   optionally cooling the aqueous solvent; and
   separating the precipitated crystalline dihydroxydiphenylsulfone.

2. A process for producing dihydroxydiphenylsulfone comprising the steps of:
   dissolving or suspending crude dihydroxydiphenylsulfone containing trihydroxytriphenylsulfone in an aqueous solvent by adding alkali;
   adjusting the pH of the aqueous solvent to 5–7 by adding an acidic substance;
   optionally cooling the aqueous solvent; and
   separating the precipitated crystalline dihydroxydiphenylsulfone.

3. The process for producing dihydroxydiphenylsulfone according to claim 1 or 2, wherein the pH is adjusted to 6 or greater and less than 7.

4. The process for producing dihydroxydiphenylsulfone according to claims 1 or 2, wherein the crude dihydroxydiphenylsulfone contains trihydroxytriphenylsulfone in a proportion of 30 wt. % or less.

5. The process for producing dihydroxydiphenylsulfone according to claims 1 or 2, wherein the crystalline dihydroxydiphenylsulfone is separated at 60° C. or lower.

6. The process for producing dihydroxydiphenylsulfone according to claim 3, wherein the crude dihydroxydiphenylsulfone contains trihydroxytriphenylsulfone in a proportion of 30 wt. % or less.

7. The process for producing dihydroxydiphenylsulfone according to claim 3, wherein the crystalline dihydroxydiphenylsulfone is separated at 60° C. or lower.

8. The process for producing dihydroxydiphenylsulfone according to claim 4, wherein the crystalline dihydroxydiphenylsulfone is separated at 60° C. or lower.

9. A method for producing dihydroxydiphenylsulfone comprising:
   dissolving or suspending crude dihydroxydiphenylsulfone containing trihydroxytriphenylsulfone in an aqueous solvent, said dihydroxydiphenylsulfone constituted of isomers;
   adjusting the pH of the aqueous solvent to 5–7 to precipitate crystalline dihydroxydiphenylsulfone; and
   recovering the precipitated crystalline dihydroxydiphenylsulfon, wherein trihydroxytriphenylsulfone and coloring impurities are separated therefrom without changing the proportion of the isomers.

10. The method according to claim 9, wherein the dissolving or suspending of the crude dihydroxydiphenylsulfone is accomplished by adding alkali.

11. The method according to claim 9, wherein the adjusting of the pH is accomplished by adding an acidic substance.

12. The method according to claim 9, further comprising cooling the aqueous solvent after the dissolving or suspending of the crude dihydroxydiphenylsulfone.

13. The method according to claim 9, wherein the pH is adjusted between 6 and 7.

14. The method according to claim 9, wherein the crude dihydroxydiphenylsulfone contains trihydroxytriphenylsulfone in a proportion of 30 wt. % or less.

15. The method according to claim 9, wherein the crystalline dihydroxydiphenylsulfone is precipitated at room temperature to 90° C.

16. The method according to claim 9, wherein the crystalline dihydroxydiphenylsulfone is recovered at 60° C. or lower.

17. The method according to claim 9, wherein the isomers are 2,4'-dihydroxydiphenylsulfone (2,4'-DDS) and 4,4'-dihydroxydiphenylsulfone (4,4'-DDS) wherein a weight ratio of 2,4'-DDS/4,4'-DDS is 0.1/99.9 to 98/2.

18. The method according to claim 9, wherein the aqueous solvent is used 0.5–10 times the crude dihydroxydiphenylsulfone.

19. The method according to claim 10, wherein the alkali is an alkali metal hydroxide.

* * * * *